United States Patent [19]
Hill et al.

[11] Patent Number: 5,148,804
[45] Date of Patent: Sep. 22, 1992

[54] DEVICE, SYSTEM, AND METHODS FOR APPLYING CRYOTHERAPY

[76] Inventors: Dennis M. Hill, 23931 SW. 25th Ct., Issaquah, Wash. 98027; Jerry L. Spence, 11308 - 101st Pl. Northeast, Kirkland, Wash. 98033

[21] Appl. No.: 546,110

[22] Filed: Jun. 28, 1990

[51] Int. Cl.$^5$ .............................................. A61F 7/00
[52] U.S. Cl. .................................. 128/402; 128/380; 128/382
[58] Field of Search .............. 128/380, 379, 400, 402, 128/403, 82.1, 399, 382; 62/530; 383/901

[56] References Cited

U.S. PATENT DOCUMENTS

| | | | |
|---|---|---|---|
| 734,213 | 7/1903 | Barnes | 128/402 |
| 3,950,158 | 4/1976 | Gossett | 128/403 |
| 4,055,188 | 10/1977 | Pelton | 128/402 |
| 4,592,358 | 6/1986 | Westplate | 128/402 |
| 4,628,932 | 12/1986 | Tampa | 128/402 |
| 4,688,572 | 8/1987 | Hubbard et al. | 128/402 |
| 4,964,402 | 10/1990 | Grim et al. | 128/402 |
| 5,016,629 | 5/1991 | Kanare | 128/402 |

*Primary Examiner*—William H. Grieb
*Assistant Examiner*—Mark S. Graham
*Attorney, Agent, or Firm*—Dean A. Craine

[57] ABSTRACT

A device, system, and methods for applying cryotherapy to a joint or body part are disclosed herein. The device comprises an adjustable wrap structure capable of wrapping at least partially around various joints or body parts. Two pockets each having an easily accessible opening manufactured on opposite sides of the wrap structure's central region on the inside surface of the wrap structure in which a cooling vehicle, such as a ice bag or a gel pack, may be inserted. A joint alignment means is manufactured on the in the central region of each device so that the device can be properly aligned and position on the joint or body part. An adjustable device attachment means is included to hold the device in place during use. The system for applying cryotherapy uses the above disclosed device and multiple sets of gel packs each set containing a coolant substance having a different freezing temperature. A method for initially applying cryotherapy that elicits less pain and a method of applying extending cryotherapy treatment are also disclosed herein.

8 Claims, 5 Drawing Sheets

DEVICE, SYSTEM, AND METHODS FOR APPLYING CRYOTHERAPY

TECHNICAL FIELD

This invention relates generally to devices, systems and methods for applying cryotherapy to an injured joint or body part. More particularly, this invention relates to devices and systems used in cryotherapy which apply cooling vehicles, such as ice bags or gel packs, to the joint and body part, and to improved methods for applying cryotherapy using the herein disclosed device and system.

BACKGROUND ART

Cryotherapy, the application of ice or other cold materials, is a proven modality for use in the initial treatment and the rehabilitation for a variety of musculo-skeletal injuries, including sprains, strains, contusions, and fractures. It has also been found to be useful in the rehabilitation process after minor surgery, such as arthroscopic surgery.

Generally, the goals of cryotherapy are to limit the formation of edema, to reduce pain, and to reduce muscle spasms. There are various types of devices, systems, and methods used today to apply cryotherapy including ice massage, ice immersion, cold whirlpools, ice bags, cold towels, cold gel packs, cold chemical packs, and vapor-coolant sprays.

It is known that clinical response to cryotherapy is improved if the cooling vehicle, such as an ice bag or gel pack, is cooled to a suitable low temperature and applied proximally to the joint or body part. The clinical response to cryotherapy is also improved if the cooling vehicle is kept sufficiently cold and applied continuously to the area during treatment. Generally, clinical response improves the longer the cooling vehicles are applied to the area. Unfortunately, most cooling vehicles generally lose their coldness in a relatively short time and must be replaced for extended treatment. Also, the application of the cold cooling vehicles for relatively long periods to the area can cause frostbite in the adjacent skin and superficial tissues. Moreover, the initial application the cooling vehicles to the skin surface often elicits a pain response which, after continuous application, gives way to an aching or throbbing sensation and then eventually to numbness.

The device and system used in the application of cryotherapy can also affect the clinical response. It is known, for example that for optimal treatment, the cooling vehicles should be positioned on opposite sides of the joint or body part so that deep, even penetration of cold treatment may be given. Many joints, however, such as the knee, elbow, ankle, and jaw, have sharp angles or protuberances which make proper alignment and placement of the device and the cooling vehicles difficult or impossible. Also, since extended cryotherapy treatment requires the continuous application of sufficiently cold cooling vehicles, several sets of sufficiently cold cooling vehicles must be on hand for exchanged in the device during treatment. Ideally, for optimal cryotherapy treatment, the cooling vehicles should be exchanged without removing the device from the joint or body part.

Heretofore, several devices have been used to apply cryotherapy to various joints and body parts using various cooling vehicles, such as ice bags or gel packs. Many of these devices, such as those disclosed in U.S. Patent Nos. 4,753,240, and 4,676,247, fail to address the problems listed above.

The present inventors have, therefore, determined that a new device, system and improved methods are needed for applying cryotherapy.

It is a general object of this invention to provide an orthopedic device that uses standard size cooling vehicles to apply cryotherapy to various joints or body parts.

It is an object of this invention to provide such a device that can be easily aligned and attached to the various joints or body parts including those having sharp angles or protuberances.

It is an object of this invention to provide such a device that disposes the cooling vehicles on substantially opposite sides of the joint or body part so that optimal therapeutic treatment may be given.

It is another object of the invention to provide a system for applying relatively long periods of cryotherapy to a joint or body part that uses the herein disclosed device.

It is further object of this invention to provide a method of applying cryotherapy which elicits little or no pain from the user when used initially.

It a still further object of this invention to provide a safe, optimal method of applying extended cryotherapy treatment.

These and other objects of the invention which will become apparent are accomplished by the device, system, and methods further described herein.

The device comprises an adjustable wrap structure made of flexible material that is capable of wrapping at least partially around various joints and body parts. In one embodiment, the wrap structure has a central region with two pockets manufactured on opposite sides thereof. Each pocket is formed by registering and attaching a flexible, thermal-conductive cover to the inside surface of the wrap structure. An extending edge of the cover is unattached to the inside surface thereby creating an easily accessible opening into each pocket.

During use, a sufficiently cooled or frozen cooling vehicle, such as an ice bag or gel pack, is placed inside each pocket and used to apply cryotherapy to the joint or body part. The position of the openings to the pockets on the inside surface of the device allows for the easy exchange of the cooling vehicle from each pocket without removing the device from the joint or body part.

A joint alignment means is located on the wrap structure's central region between the two pockets. The joint alignment means allows the device to be properly positioned and aligned on various joints or body parts. It is especially useful on angled joints or body parts or those having protuberances which make positioning and alignment of typical devices difficult. The joint alignment means comprises an opening or passage which enables the wrap structure to be aligned on the joint or body part so that the pockets are disposed on substantially opposite sides of the joint or body part for optimal cooling. Although the joint alignment means may be manufactured in any shape, in one embodiment disclosed herein, it comprises a circular passage through which the vertex or protuberances of the joint or body part may be partially extended.

A device attachment means is attached to the wrap structure for adjustably securing the device to the joint or body part. The device attachment means comprises at least one elastic strap permanently attached at one end to an edge of the wrap structure or pocket. During use, the opposite, detachable end of the strap is placed around the joint or body part and adjustably connected to the outside surface of the wrap structure located on the opposite side of the device. In one embodiment, the strap is made of elastic material which enables the device to be pulled slightly from joint or body part surface so that the cooling vehicles may be more easily removed and exchanged.

A strap attachment means is used to adjustably connect the detachable end of each strap to the wrap structure's opposite outside surface. In one embodiment, the strap attachment means comprises a pad-shaped hook connector and a pad-shaped loop connector disposed between the detachable end of the strap and the wrap structure's outside surface.

A system and improved methods for applying cryotherapy using the above described device is also disclosed herein. It has been discovered that the temperature of a joint or body part may be adjusted by exchanging different sets of gel packs, each having different freezing and cooling properties, in the device during treatment. The freezing and cooling property of the gel packs may be changed by altering the chemical composition of the coolant substance contained in each gel pack.

The system uses two or more sets of standard size gel packs placed inside each pocket during use. The gel packs containing a coolant substance comprised by volume; 0.5% to 2% polymer gel, 3 to 10% glycerin, and 88 to 96.5% water. The compositions of each coolant substance is adjusted within the above ranges so that each set of two gel packs freezes at a different temperature below 32 degrees F. The first set of gel packs contains a coolant substance comprising by volume 1% polymer gel, 3% glycerin, and 96% water and freezes at approximately 28 degrees F. The second set of gel packs contains a coolant substance comprising by volume 1% polymer gel, 7% glycerin, and 92% water and, freezes at approximately 21 degrees F. An optional third set of gel packs contains a coolant substance comprising by volume 1% polymer gel, 10% glycerin, and 89% water, and freezes at approximately 10 degrees F.

Prior to use, all of the gel packs are stored at a temperature below the freezing temperature of the lowest freezing gel pack. It is known that the lowest possible temperature of a gel pack is limited by the freezing temperature of the coolant substance contained therein. This property allows every set of gel packs to be conveniently stored at a very low temperature in one freezer until needed. Since each gel pack is made of transparent material, a dye substance may be added to each coo substance so its freezing properties may be easily determined.

The improved method of initial applying cryotherapy that elicits less pain when initially applied by gradually lowering the skin temperature of the joint or body part. The improved method comprises the following steps: (1) selecting and attaching a properly fitting device which can hold two attached gel packs on substantially opposite sides of the joint; (2) selecting a frozen first set of gel packs containing a coolant substance having a freezing temperature of approximately 30 degrees F.; (3) placing one gel pack from the first set of gel packs into each pocket for approximately twenty to sixty minutes; (4) removing the first set of gel packs from each pocket; (5) selecting a frozen second set of gel packs containing a coolant substance having a freezing temperature of approximately 25 degrees F.; (6) placing one gel pack from the second set of gel into each pocket for approximately twenty to sixty minutes; (7) keeping each gel pack from the second set of gel packs in each pocket until cryotherapy treatment is completed, and; (8) removing the device from the joint.

An improved method for applying extended cryotherapy treatment to a joint is also disclosed using multiple sets of gel packs which lower and raise the skin temperature of the joint or body part during treatment. The improved method comprises the following steps: (1) selecting and attaching a properly fitting device which can hold at least two attached gel packs on substantially opposite sides of a joint; (2) selecting a frozen set of first set of gel packs containing a coolant substance having a freezing temperature of approximately 30 degrees F.; (3) placing one gel pack from the first set of gel packs into each pocket on the device so that each gel pack is disposed on substantially opposite sides of the joint; (4) keeping the device attached to the joint continuously until the temperature of the skin located immediately around the joint is between 40 and 45 degrees F.; (5) exchanging the first set of gel packs with a frozen second set gel packs containing a coolant substance having a freezing temperature of approximately 25 degrees F.; (6) keeping the device attached to the joint continuously until temperature of the skin located immediately around the joint is between 30 to 40 degrees F.; (7) removing the second set of gel packs from each pocket; (8) repeating steps 3 through 7 for 3 to 24 hours or until swelling or pain is reduced, and; (9) removing the device from the joint.

For special conditions and applications, a frozen third set of gel packs containing coolant substance with a freezing temperature of approximately 18 degrees F. may be used for 15 to 30 minutes between steps (7) and (8) for further cooling.

BRIEF DESCRIPTION OF DRAWINGS

These and other advantages of the present invention may be appreciated from studying the following detailed description of the preferred embodiment together with the drawings in which.

BEST MODE FOR CARRYING OUT THE INVENTION

The present invention disclosed and claimed herein comprises a portable device, generally referred to as 12, used to apply cryotherapy to various joints or body parts 13, (hereinafter referred generally as joint 13). Also disclosed and claimed herein is a system for applying cryotherapy comprising the device 12 and two or more sets of gel packs and two improved methods for applying cryotherapy treatment using the above system. Although the following invention will be described in its preferred embodiment for use on humans, it should be understood that device 12, system, and the methods disclosed herein may be used with other animals. As shown generally in FIG. 1, device 12 is used to apply cryotherapy to a joint 13 by applying two cooling vehicles 44, such as an ice bag or gel pack (hereinafter generally referred to as cooling vehicle 44), contained in two pockets to the skin surface of various joints 13. Device 12 comprises a wrap structure 14 that is able to wrap at least partially around the joint 13. Two pockets 30 are manufactured on the inside surface 15 of wrap structure 14 on opposites sides the wrap structure's 14 central region 32. A joint alignment means comprising a circular passage 34 is manufactured on central region 32 which enables the vertex or protuberance of the joint to partially extend through so that device 12 may be properly positioned and aligned when used on the joint 13. A device attachment means comprising straps 35 are used to hold device 12 in place around the joint 13.

Figure 2:
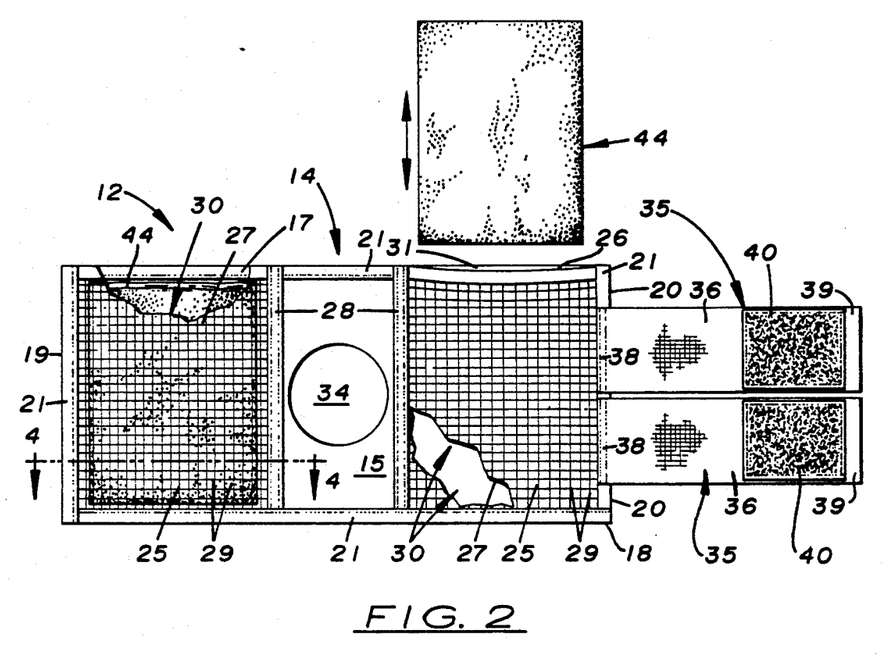
FIG. 2 is a front plan view of the preferred embodiment of the present invention illustrating the inside surface of the wrap structure with two cooling vehicles being inserted into the pockets.
Figure 3:
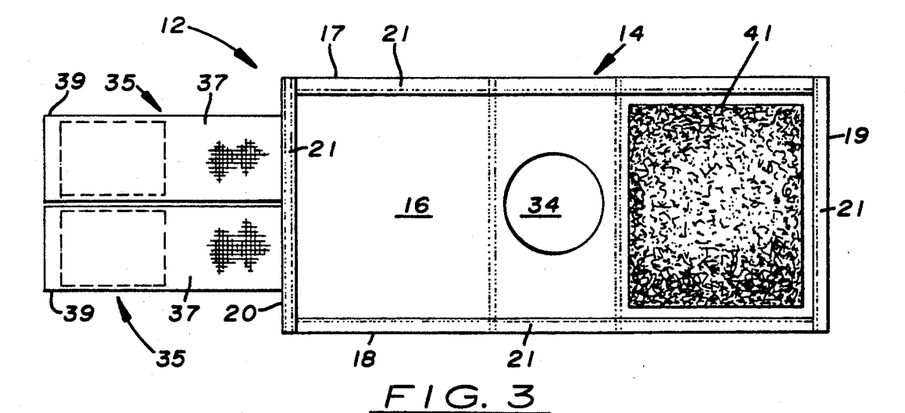
FIG. 3 is a rear plan view of the preferred embodiment of the present invention illustrating the outside surface of the wrap structure shown in FIG. 2.

As shown in greater detail in FIGS. 2-3, wrap structure 14 is rectangular-shaped and made of flexible material, such as cotton or nylon. Wrap structure 14 has an inside surface 15, an outside surface 16, upper and lower horizontal edges, 17, and 18, respectively, and first and second vertical edges, 19 and 20, respectively. The edges 17-20 may be covered with binding tape 21 which provides a finished appearance and keeps the wrap structure's flexible material from unraveling.

Figure 4:
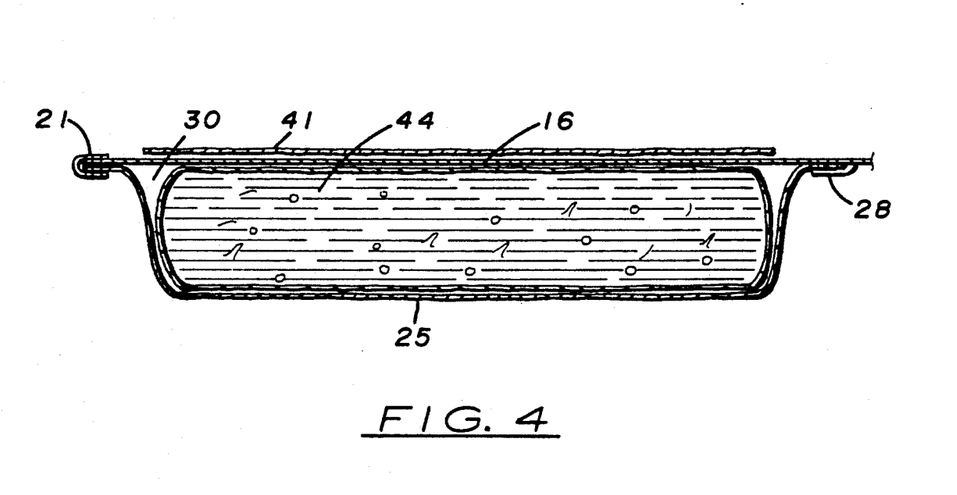
FIG. 4 is a sectional view taken along lines 4—4 in FIG. 1 illustrating a cooling vehicle, positioned inside a pocket.

Each pocket 30 is formed on wrap structure 14 by registering and attaching three edges of a cover 25 to the inside surface 15. Binding tape 28 may be attached to the three edges to secure them to inside surface 15. The extending edge 26 of each cover 25 is unattached thereby creating an easily accessible opening 31 into each pocket 30. Each cover 25 is made of thin, lightweight, flexible, thermal conductive material. In the preferred embodiment, cover 25 is made of thin nylon mesh material with mesh openings 29 approximately ⅛ inch in diameter. As shown in FIG. 4, during use, a cooling vehicle 44 is placed inside each pocket 30. The mesh openings 29 of cover 25 allow each cooling vehicle 44 to partially touch the skin surface so that maximum cooling treatment is given.

Located centrally on central region 32 is a joint alignment means which allows device 12 to be properly positioned and aligned on the joint 13. In the preferred embodiment, the joint alignment means comprises a circular passage 34 located approximately equal distance between each pocket 30. As discussed further below and as shown in FIGS. 10(a)-(d), during use, the vertex or protuberance of various joints 13 may be partially extended through circular passage 34 so that pockets 30 are disposed on substantially opposite sides of joint 13.

Figure 1:
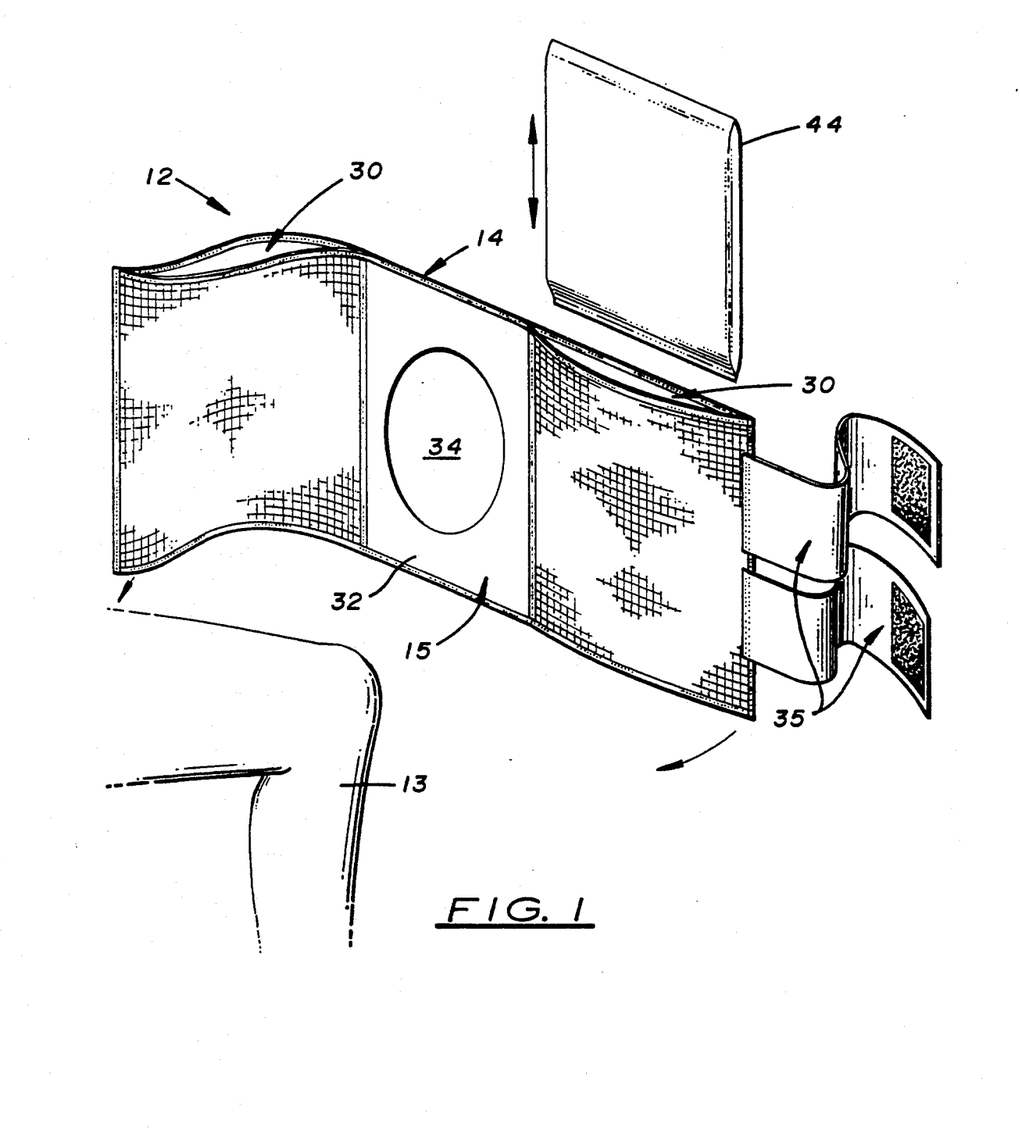
FIG. 1 is a perspective view of the preferred embodiment of the present invention.

A device attachment means is attached to wrap structure 14 to adjustably secure it to the joint 13. As seen in FIGS. 1-3, in the preferred embodiment, the device attachment means comprises two adjustable straps 35 permanently attached at an attached end 38 to edge 20 of wrap structure 14. Each strap 35 is substantially rectangular-shaped made of elastic nylon material with an opposite detachable end 39 and an inner and outer surfaces 36 and 37, respectively. Each strap 35 extends substantially perpendicular from edge 20 and spaced approximately equal distance from its nearest upper or bottom horizontal edge 17 and 18, respectively.

Figure 5:
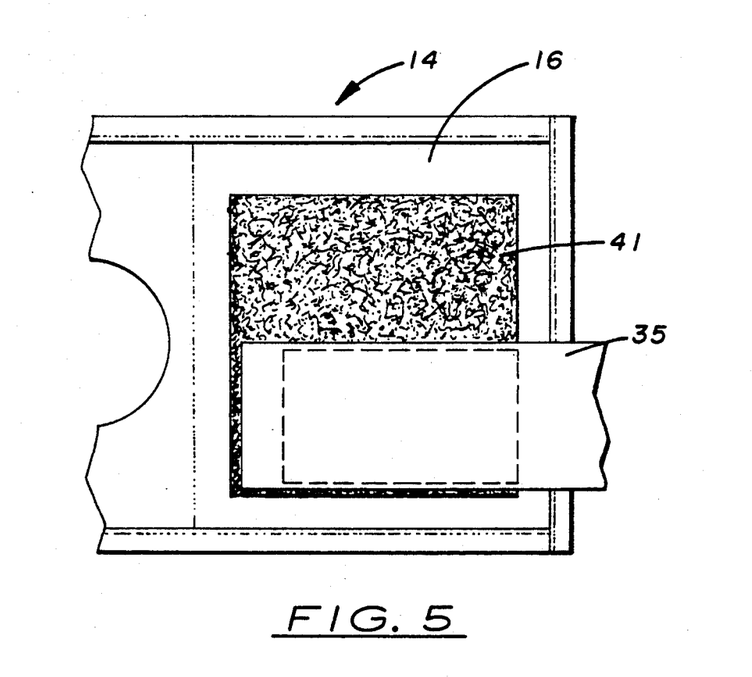
FIG. 5 is a partial, rear plan view illustrating the outside surface of the wrap structure having a strap adjustably attached to the outside surface with hook and loop connectors.

A strap attachment means is disposed between the detachable end 39 of each strap 35 and the outside surface 16 of wrap structure 14 so that strap 35 may be adjustably connected to outside surface 16 when device 12 is wrapped around a joint 13. In the preferred embodiment, the strap attachment means comprises a pad-shaped, hook connector 40 (trademark "VELCRO" connector) attached to inner surface 36 near detachable end 39 as shown in FIGS. 1-2. As shown in FIGS. 3 and 5, a large, complimentary pad-shape, loop connector 41 (trademark "VELCRO" connector) is attached to the outside surface 16 of wrap structure 14 near vertical edge 19. During use, the two hook connectors 40 on each strap 35 and the loop connector 41 are interconnected to adjustably connect the detachable ends 39 of straps 35 to outside surface 16. Hook connectors 40 are independently interconnected to loop connector 41 which allows them to be adjusted for different joints 13.

Device 12 may be manufactured in different sizes for use on adults or children. For example, for use on adults, wrap structure 14 measures approximately 6 inches (H)×13 inches (W) with central region 32 measuring approximately 6 inches (H)×3 inches (W). Each pocket 30 measures approximately 6 inches (H)×5 inches (W) and will hold a cooling vehicle 44 that measures approximately 5 inches (H)×4 inches (W). Circular passage 34 located on central region 32 measures approximately 2 ¼ inches in diameter. Each strap 35 measures approximately 2 inches (W)×9 inches (L) with hook connectors 40 each measuring approximately 1 ¾ inches (H)×3 ¼ inches (W). Loop connector 41 measures approximately 4 inches (H)×4 inches (W).

For use on smaller adults and teenagers, device 12 is manufactured proportionately smaller with wrap structure 14 measuring approximately 5 inches (H)×11 inches (W). Central region 32 measures approximately 5 inches (H)×'¼ inches (W). Each pocket 30 measures approximately 5 inches (H)×4 ¼inches (W) and will hold a cooling vehicle bag 44 that measures approximately 4 inches (H)×3 inches (W). The circular passage 34 located on central region 32 measures approximately 2 inches in diameter. Each strap 35 measures approximately 2 inches (H)×7 inches with hook connectors 40 each measuring approximately 1 ½ inches (H)×2 ½ inches (W) Loop connectors 41 measure approximately 3 inches (H) and 3 inches (W).

For use on children, device 12 is manufactured proportionately smaller with wrap structure 14 measuring approximately 4 inches (H)×9 inches (W). Central region 32 pocket 30 measures approximately 4 inches (H)×3 ½ inches (W) and will hold a cooling vehicle 44 that measures approximately 3 inches (H)×2 inches (W). Circular passage 34 measures approximately 1 ½ inches in diameter. Each strap structure 35 measures approximately 1 ½ inches (H)×6 inches with hook connectors 40 each measuring approximately 1 ½inches (H)×2 inches (W). Loop connector 41 measures approximately 2 inches (H)×2 inches (W).

Figure 6:
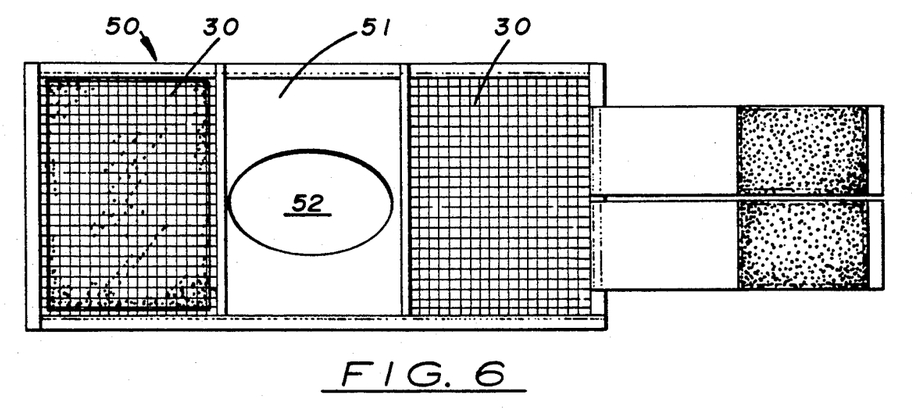
FIG. 6 is a front plan view of a second embodiment of the invention.
Figure 7:
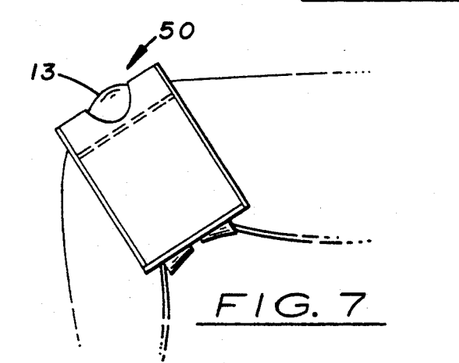
FIG. 7 is an elevation view illustrating the second embodiment shown in FIG. 6 attached to a knee.

In FIGS. 6-7, a second embodiment of the invention is illustrated with device 50 having a modified joint alignment means that may be useful in certain applications. Device 50 has a two pockets 30 on opposite sides of central region 51 which is slightly larger than central region 32 on device 12. Circular passage 34 on device 12 is replaced with an oval passage 52 which provides greater access to the joint 13 along the device's 50 longitudinal axis. In other embodiments, (not shown) oval passage 52 may be rotated so that greater access is provided across the device's transverse axis. Oval passage 52 provides greater access to surface of joint 13, which allows one to perform minor surgery, such as arthroscopic surgery, on joint 13 while device 50 is attached. By this manner, cryotherapy can be applied earlier to the joint 13 than with other commonly used devices or methods to reduce pain and swelling.

Figure 8:
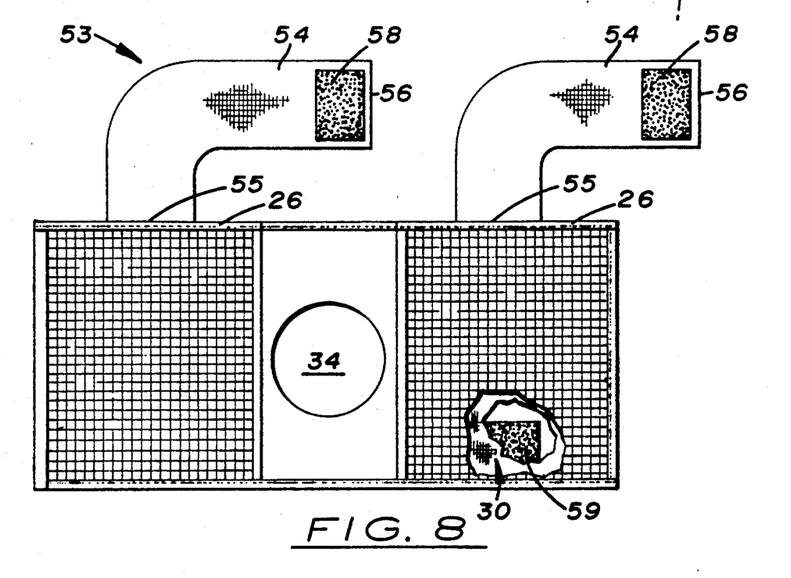
FIG. 8 is a front plan view of a third embodiment of the invention.
Figure 9:
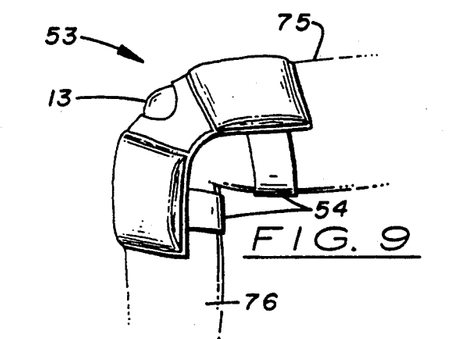
FIG. 9 is an elevation view illustrating the third embodiment shown in FIG. 8 attached to a knee.

FIGS. 8-9 illustrate a third embodiment of the invention that also may be useful for special applications. In some situations, it may be desirable to apply a pair of cooling vehicles 44 above and below the joint 13 rather than on opposite sides of the joint. Device 53 is designed for this purpose. Device 53 has two elongated straps 54 that extend laterally from edge 26 of device 53. Elongated straps 54 are connected at attached end 55 and extended perpendicular from the extending edge 26 of each pocket 30. During use, cooling vehicles (not shown) are placed in each pocket 30 and elongated straps 54 are wrapped around the adjacent limb structures 75, 76, (shown above and below joint 13, respectively) to adjustably secure device 53 to the joint 13. Elongated straps 54 are made of nylon, elastic material similar and slightly longer than straps 35 used on device 12 so that straps 54 can be wrapped around the larger limb structures 75 and 76. During use, detachable end 56 of each strap 54 is adjustably connected to the outside surface (not shown) on device 53 opposite edge 26 of pocket 30. Hook and loop connectors 58 and 59, respectively, are disposed between each detachable end 56 and outside surface to adjustably secure each strap 54 in place during use.

As shown in FIG. 10(a)-(d), the device 12 may be used on different joints—elbow 90, ankle 93, knee 96 and jaw 99, respectively. In each application, the cooling vehicles 44 located in each pocket 30 are disposed on substantially opposites sides of each joint 90, 93, 96, and 99 for optimal cooling effect. The circular opening 34 is of sufficient size so that vertex or protuberance 91, 94, 97, and 100 of each joint 90, 93, 96, and 99, respectively, may partially extend through.

The location of each opening 31 near upper horizontal edge 17 and the elastic nature of straps 35 allow the cooling vehicles 44 to be easy and quickly exchanged during use. In most situations, it is not necessary to remove device 12 from the joint 13 while removing and exchanging the cooling vehicles 44. If one strap 35 is loosened or disconnected, device 12 while remain in proper position and alignment during the removal and exchange process.

When treatment is completed, device 12 is removed from joint 13 by disconnecting hook and loop connectors 40 and 41, respectively. Device 12 may be reused after washing with hot soap and water.

Device 12 has been shown to be effective in applying cryotherapy post-surgically and in the treatment of joint and muscle injuries. It should be understood, however, that device 12 may also be used in heat therapy for treatment of chronic conditions such as rheumatoid arthritis, bursitis, and osteoarthritis.

Figures 10A, 10B, 10C, 10D, 11:
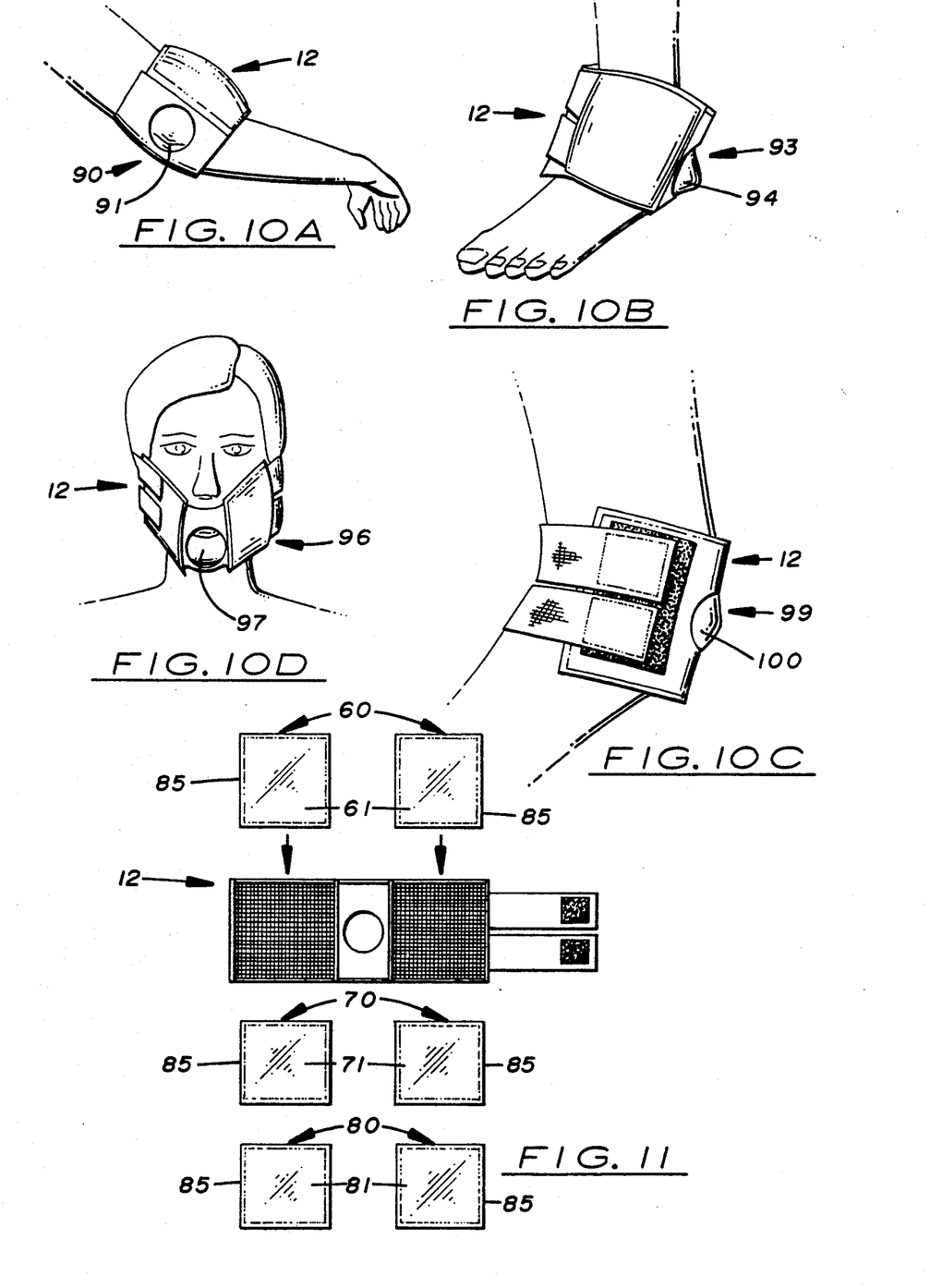
FIG. 10(a) is an illustration of the device used on an elbow joint.
FIG. 10(b) is an illustration of the device used on an ankle joint.
FIG. 10(c) is an illustration of the device used on a knee joint.
FIG. 10(d) is an illustration of the device used around the jaw.
FIG. 11 is an illustration showing a system for applying cryotherapy comprised of the above disclosed device and a first, second, and optional third set of gel packs capable of being used and exchanged in the device during use.

Also disclosed herein is a system for applying cryotherapy comprising device 12 and two or more sets of gel packs 60, 70, and 80 as shown in FIG. 11 Each set of gel packs 60, 70, and 80 includes two standard size gel packs each manufactured to fit closely into pocket 30. Each set of gel packs 60, 70, and 80 contains a coolant substance, 61, 71, and 81, respectively, which has different freezing and cooling properties. Each gel pack 60, 70, and 80, is prepared by placing coolant substance 61, 71, and 81 into a transparent bag 85 made of polyethylene - nylon blend. Each bag 85 is filled approximately 85% and sealed in an air tight fashion.

For devices 12 used on adults, each bag 85 measures approximately 5 ¼ inch (W)×5 ¾ inch (H) which enables it to fit securely into pocket 30. For device used on small adults and children, bags 85 are manufactured proportionately smaller to fit closely into the smaller pockets 30.

The coolant substances 61, 71, and 81 are semi-flexible gel-like substance which, when frozen, can be easily molded around the joint. Coolant substances 61, 71, and 81 comprise by volume: 0.5% to 2% polymer gel; 3% to 10% glycerin, and 88% to 96.5% water. The polymer gel is proprietary and is known to be an adsorbent copolymer made of acrylamide acrylate material available from the May River Corporation located in Jacksonville, Fla. It is available in both a granular and a powder form and is referred to as "MRC 770". When water is added, it is sold by Mary River Corporation under the trademark "ICE BURG COLD PAK". In the preferred embodiment, the granular formulation is used with the granules measuring between 1/32 to 3/16 inch in diameter.

The ingredients of each coolant substance 61, 71, and 81 is adjusted within the above stated ranges so each set of two gel packs freezes at a different temperature below 32 degrees F. The first set of gel packs 60 contains a coolant substance 61 comprising by volume 1% polymer gel, 3% glycerin, and 96% water and freezes at approximately 30 degrees F. The second set of gel packs 70 contains a coolant substance 71 comprising by volume 1% polymer gel, 7% glycerin, and 92% water and freezes at approximately 25 degrees F. An optional third set of gel packs 80 contains a coolant substance 81 comprising by volume 1% polymer gel, 10% glycerin, and 89% water, and freezes at approximately 18 degrees F.

When frozen, the surface temperature of gel pack 60 is approximately 30 degrees F. which can be maintained for approximately seven and one-half hours at room temperature. When used and applied to a knee, the skin surface of the knee is lowered between 40 to 45 degrees F. in approximately 30 minutes and can be maintained at this temperature for approximately ten hours.

The surface temperature of each gel pack 70 containing coolant substance 71 when frozen is approximately 25 degrees F. which can be maintained at room temperature for approximately three hours. When used with the device 12 and placed around a knee, gel packs 70 will lower the temperature of the skin surface to approximately 32 degrees F. up to approximately three hours. The surface temperature of each gel pack 80 is approximately 18 degrees F. which can be maintained at room temperature for approximately two hours. When used in device 12 and applied to a knee joint, the skin surface of the joint is lowered to approximately 20 degree F. which may be maintained for approximately four hours. Since damage due to frostbite is likely to occur when using gel packs 80, application is usually only for 15 to 30 minutes.

Prior to use, the sets of the gel packs 60, 70, and 80 are stored together at a temperature below the freezing temperature of the lowest freezing gel pack. It is known that the lowest possible temperature of a gel pack is limited by the freezing temperature of the coolant substance contained therein. This known property allows one to conveniently store all of the sets 60, 70, and 80 in one conveniently location at a very low temperature until needed. Since each gel pack is made of transparent material, a dye substance may be added to each coolant substance 61, 71, and 81, to indicate its freezing and cooling properties.

Using the above disclosed system, a method of initially applying cryotherapy that is less painful and a method of applying extended cryotherapy treatment are disclosed herein.

The method of initially applying cryotherapy to a joint is less painful comprising the following steps: (1) selecting and attaching a properly fitting a device which can hold two attached gel packs on substantially opposite sides of the joint; (2) selecting a frozen first set of gel packs containing a coolant substance having a freezing temperature of approximately 30 degrees F.; (3) placing one gel pack from the first set of gel packs into each pocket for approximately twenty to sixty minutes; (4) removing the gel packs from the first set of gel packs from each pocket; (5) selecting a frozen second set of gel packs containing a coolant material which freezes at approximately 25 degrees F. (6) placing one gel pack from the second set of gel into each pocket for approximately twenty to sixty minutes (7) keeping each gel pack from the second set in each pocket until cryotherapy treatment is completed, and: (8) removing the device from the joint.

Using the above described gel packs, a method for applying extended cryotherapy to a joint is also disclosed comprising the following steps: (1) selecting and attaching a properly fitting device which can hold two attached gel packs on substantially opposite sides of a joint; (2) selecting a frozen set of first set of gel packs containing a coolant substance having a freezing temperature of approximately 30 degrees F., (3) placing one gel pack from the first set of gel packs into each pocket on the device so that each gel pack is disposed on substantially opposite sides of the joint; (4) keeping the device attached to the joint continuously until the temperature of the skin located immediately around the joint is between 40 and 45 degrees F.; (5) exchanging the first set of gel packs with a frozen second set gel packs containing a coolant substance that freezes at approximately 25 degrees F; (6) keeping the device attached to the joint continuously until temperature of the skin located immediately around the joint is between 30 to 40 degrees F.; (7) remove the second set of gel packs from each pocket; (8) repeating steps 3 through 7 for 3 to 24 hours or until swelling or pain is reduced, and; (9) removing the device from the joint.

For special conditions and applications, a frozen third set of gel packs having a coolant substance that freezes at approximately 18 degrees F. may be used between steps (7) and (8) for further cooling. The third set of gel packs is usually used for short periods only or until the skin located immediately around the joint is between 25 and 30 degrees.

INDUSTRIAL APPLICABILITY

This invention will find use in the practice of medicine generally and, more particularly, in the fields of orthopedics and sports medicine. It may also find application in the dental industry and possibly, veterinarian medicine. The present invention discloses a device and system for optimally applying cryotherapy, method for applying extended cryotherapy treatment, and a method of initially applying cryotherapy which elicits little or no pain.

In compliance with the statute, the invention has been described in language more or less specific as to structural features. It should be understood, however, that the invention is not limited to the specific features shown, since the means and construction shown comprised preferred forms of putting the invention into effect. The invention is, there fore, claimed in any of its forms or modifications within the legitimate and valid scope of the amended claims, appropriately interpreted in accordance with the doctrine of equivalents.

We claim:

1. A device used to apply cryotherapy, comprising:

a) a rectangular-shaped wrap structure capable of being at least partially wrapped around a joint, said wrap structure having a central region, a first and second vertical edge, and an upper and lower horizontal edge, said wrap structure being made of a single sheet of flexible material and having an inside and an outside surface;

b) two pockets formed on said inside surface of said wrap structure, each said pocket being located on opposite sides of said central region, each said pocket being formed by attaching a cover made of thin, flexible mesh material, said mesh material having openings with a sufficient diameter to enable a portion of a gel pack inserted into each said pocket to touch the skin surface around said joint, and to make said mesh material sufficiently flexible to enable the insertion or removal of said gel pack from said pocket during use, each said pocket having an unattached extending edge thereby creating an opening into each said pocket;

c) two gel packs, one said gel pack being placed into each said pocket;

d) a passage located on said central region and approximately equal distance between said pockets, said passage having a sufficient size and shape to enable a portion of said joint to be partially extended through so that said device is aligned on said joint with said cooling vehicles disposed on substantially opposite sides of said joint when said device is attached to said joint;

e) two elastic straps having an attached end and a detachable end, said attached end being permanently attached to said second vertical edge of said wrap structure, each said strap capable of being placed around said joint and adjustably connected to said outside surface of said wrap structure on the opposite side of said device, said elastic straps having a sufficient length so that said pockets are disposed on substantially opposite sides of said joint when said device is attached to said joint and;

f. a pad-shaped hook connector attached to said inner surface of each said strap near said detachable end, and;

g. a pad-shaped loop connector located on said outside surface of said wrap structure on said side of wrap structure near said first vertical edge, said pad-shaped loop connector being capable of releasably engaging said pad-shaped hook connector on each said strap to adjustable connect each said detachable end of each said strap thereto.

2. A device as claim 1, wherein said mesh material has mesh openings approximately ⅛ inch in diameter.

3. A device of claim 2, wherein said passage is substantially circular and measures approximately 2 ½ inches in diameter.

4. A device of claim 2, wherein said passage is substantially circular and measures approximately 2 inches in diameter.

5. A device of claim 2, wherein said passage is substantially circular and measures approximately 1 ½ inches in diameter.

6. A device of claim 2, wherein said passage is sufficiently oval in shape to enable said device to be positioned and aligned on said joint and to allow access to the area surrounding said portion of said joint protruding through said passage when said device is used.

7. A device used to apply cryotherapy, comprising:

a) a rectangular-shaped wrap structure capable of being at least partially wrapped around a joint, said wrap structure having a central region, a first and second vertical edge, and an upper and lower horizontal edge, said wrap structure being made of flexible material and having an inside and an outside surface;

b) two pockets formed on said inside surface of said wrap structure, each said pocket being located on opposite sides of said central region, each said pocket having an unattached extending edge thereby creating an opening into each said pocket;

c) two cooling vehicles, one said cooling vehicle being placed into each said pocket;

d) a passage located on said central region and approximately equal distance between said pockets, said passage having a sufficient size and shape to enable a portion of said joint to be partially extended through so that said device is aligned on said joint with said cooling vehicles disposed on substantially opposite sides of said joint when said device is attached to said joint;

e) two straps attached to said wrap structure to adjustable secure said device to said joint, each said strap is made of elastic material, extends laterally from said device, and has a detachable end, each said strap being permanently attached to one said extending edge of one said pocket, each said strap is elongated and capable of being wrapped around a limb structure located adjacent to said joint to adjustable secure said device to said joint, and;

f) a strap attachment means disposed between said detachable end of each said strap and said outside surface of said wrap structure which enables each said detachable end to be adjustably connected to said outside surface.

8. A device of claim 7, wherein said strap attachment means is a pad-shaped hook connector attached to said detachable end of each said strap, and wherein a pad-shaped loop connector is attached to said outside surface of said wrap structure opposite said pocket with said strap permanently attached thereto.

* * * * *